(12) United States Patent
Kato et al.

(10) Patent No.: US 7,531,057 B2
(45) Date of Patent: *May 12, 2009

(54) METHOD FOR PRODUCING BIOCHEMICAL ANALYSIS UNIT

(75) Inventors: Akifumi Kato, Kanagawa (JP); Kenji Nakajima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 677 days.

This patent is subject to a terminal disclaimer.

(21) Appl. No.: 10/354,994

(22) Filed: Jan. 31, 2003

(65) Prior Publication Data

US 2003/0143523 A1 Jul. 31, 2003

(30) Foreign Application Priority Data

Jan. 31, 2002 (JP) ............................. 2002-024233

(51) Int. Cl.
*B32B 37/00* (2006.01)
(52) U.S. Cl. .................... 156/261; 156/269; 156/555; 156/582; 156/583.1
(58) Field of Classification Search ................ 156/250, 156/256, 261, 269, 555, 580, 582, 583.1
See application file for complete search history.

(56) References Cited

U.S. PATENT DOCUMENTS

| | | | | |
|---|---|---|---|---|
| 4,493,815 | A * | 1/1985 | Fernwood et al. ........... | 422/101 |
| 5,080,747 | A * | 1/1992 | Veix ........................... | 156/352 |
| 5,380,644 | A | 1/1995 | Yonkoski et al. | |
| 5,807,522 | A | 9/1998 | Brown et al. | |
| 6,171,780 | B1 * | 1/2001 | Pham et al. .................... | 435/4 |
| 2001/0026917 | A1 | 10/2001 | Neriishi et al. | |
| 2002/0094533 | A1 * | 7/2002 | Hess et al. ..................... | 435/6 |
| 2002/0197568 | A1 * | 12/2002 | Neriishi et al. .............. | 430/496 |

FOREIGN PATENT DOCUMENTS

| | | |
|---|---|---|
| EP | 1 023 955 A1 | 8/2000 |
| EP | 1 267 169 A2 | 12/2002 |
| JP | 58-69281 | 4/1983 |
| JP | 59-56479 | 3/1984 |
| JP | 59-75200 | 4/1984 |
| JP | 60-101179 | 6/1985 |
| JP | 62-170950 | 7/1987 |
| JP | 63-188135 | 8/1988 |
| JP | 1-60782 | 12/1989 |
| JP | 1-60784 | 12/1989 |
| JP | 2-276997 | 11/1990 |
| JP | 4-3952 | 1/1992 |
| JP | 6-301140 | 10/1994 |

OTHER PUBLICATIONS

Japanese Abstract No. 20011160684, dated Jun. 12, 2001.

* cited by examiner

*Primary Examiner*—James Sells
(74) *Attorney, Agent, or Firm*—Sughrue Mion, PLLC

(57) ABSTRACT

A continuous substrate and a continuous absorptive sheet are fed to a press station, and pressed continuously or intermittently. Part of the continuous absorptive sheet is charged in plural holes formed in the continuous substrate to form a biochemical analysis sheet. The biochemical analysis sheet is cut into predetermined tips to obtain a biochemical analysis unit.

21 Claims, 8 Drawing Sheets

METHOD FOR PRODUCING BIOCHEMICAL ANALYSIS UNIT

BACKGROUND OF THE INVENTION

1. Field of the Invention

The present invention relates to a method for producing a biochemical analysis unit, and particularly to a method for producing a biochemical analysis unit which prevents to cause a noise when a labeling substance or a fluorescent substance radiates or emits a light.

2. Description Related to the Prior Art

As disclosed in Japanese Patent Publications No. 1-60784, 1-60782, and 4-3952, an auto radiography image analyzing system is known for detecting a radioactive labeling substance which are dosed with a living organism. In the auto radiography image analyzing system, a part of the living organism on dosage of the labeling substance is used as a sample. When the sample overlaps for a predetermined time with a stimulable phosphor sheet having a stimulating phosphor layer, the energy of radiation irradiated from the radioactive labeling substances is accumulated and recorded in the stimulable phosphor layer. Thereafter when the stimulable phosphor layer is scanned in an electromagnetic wave, the stimulable phosphor is excited, and a stimulation light emitted from the stimulable phosphor layer is photoelectrically detected. Thus a detection data is obtained and effected in image processing for forming an image on a display, such as a CRT or the like, or a recording material.

In the auto radiography image analyzing system, a development processing is not necessary. Further the image data obtained from the detection data can be processed to reproduce a desired image and therefore a quantity analysis becomes possible with a computer.

Further, recently, an analyzing system is known for analyzing a substances derived from living organism, for example, a nucleic acid (such as DNA and RNA), proteins and the like. In the analyzing system, the substance derived from living organism that is labeled with a labeling substance is set in the electromagnetic waves for exiting the labeling substance. Thus the excited light is generated and detected such that the detecting data is obtained to form the image.

As the analyzing system, there are a fluorescent analyzing system, a chemiluminescence analyzing system and the like.

In the fluorescent analyzing system is carried out the determination of genetic sequence, expression level of gene, routs of metabolism, absorbance and discharge, the separation or the identification of protein, the estimation of molecular weight or properties of protein, or the like. The substance derived from living organism, such as protein, is labeled with the fluorescent substances by dipping a gel support in a solution containing a fluorescent substance after the gel support on which a plurality of proteins are distributed by means of electrophoresis. When the sample is excited with the exciting light, then a fluorescent light generated from the fluorescent substance is detected to form an image. Thus positions and amount distributions of proteins on the gel support can be known. The fluorescent analyzing system has a merit in that the radioactive substance is not used, and that the genetic sequence and the like are easily determined.

In the fluorescent analyzing system, a western blotting method and a southern blotting method may be used. In the western blotting method, a part of proteins after electrophoresis is transferred to a solid base such as nitrocellulose sheet from the gel support. Then, an antibody which makes a selective reaction with the substance of living organism to be detected is labeled with the labeling substance such as fluorochrome to produce a probe. When the probe and the protein are combined, the protein is selectively labeled. The positions or the quantitative distribution of protein on the solid base can be detected by sensing a fluorescent light from the fluorochrome which is excited with exciting light. The western blotting method is also used for searching a distribution of DNA in a DNA segment.

In the southern blotting, after a plurality of DNA fragments on a gel support is distributed by means of electrophoresis and denaturated, at least a part of DNA fragments is transferred onto a transfer support such as nitrocellulose support. The denaturated DNA fragments are hybridized with a probe in which a fluorescent dye labels DNA or RNA complementary to the denaturated DNA fragments. In the hybridization, only the target DNA fragments are selectively labeled. When the fluorescent dye is excited, then the distribution of the target DNA on the transfer support is detected. Further, it is preferable to use the enzyme. In this case, the compremntary DNA is combined with the enzyme, and contacted to the fluorescent substrate, and the fluorescent substrate is transformed to the fluorescent substance. Then the fluorescent light irradiated from the fluorescent substance is sensed to detect the distribution of the target DNA.

In the chemiluminescent analyzing system, the labeling substance is used, which generates a visible chemiluminescent light by contacting to the chemiluminescent substrate. The substance fixed on a support is selectively labeled with the labeling substance, and thereafter contacted to the chemiluminescent substrate to emit the chemiluminescent light which is photometry detected.

Recently, there is known a micro array analyzing system. In the micro array analyzing system, a specific binding substance is used, which can be bound with the substance derived from living organism, such as hormone, tumor marker, enzyme, antibody, antigen, abzyme, other protein, nucleic acid, cDNA, DNA, RNA or the like. According to the specific binding substance are established sequence, base length, composition and the like.

In the micro array analyzing system, the several substances labeled with a labeling substance are spotted at different positions on a surface (glass plate, porous membrane and the like) of the biochemical analysis unit. The substances are combined with the specific binding substance previously spotted by a spotting device, and labeled with the labeling substance or the luminescent substance for producing the micro array. When the exciting light is irradiated, a light (such as luminescence) is generated by a labeling substance in the micro array and photoelectrically detected.

Further, an improvement of the micro array is used with the radioactive labeling substance for labeling the substance of living organism that is bounded with the specific binding substance. The micro array is superposed on the stimulable phosphor sheet to make an exposure of the stimulating phosphor layer. Then the exciting light is impinged on the stimulating phosphor layer, and the stimulation light emitted from the stimulating phosphor layer is photoelectrically detected.

According to the micro array image analyzing system, several sorts of the specific binding substance are formed as spots in high density. After labeled with the labeling substance, the substance derived from living organism is dropped on the spots to hybridize with the specific binding substance. Thus the analysis of the substance derived from the living organism is made in a short time.

In the above mentioned image analyzing system for micro array is used a biochemical analysis unit in which a micro array is formed on a support (or base), such as a glass plate, a membrane or the like. The micro array has plural spots for detecting plural kinds of materials. However, in the biochemical analysis unit as the electromagnetic wave or the light generated from the labeling substance in the neighboring spots is mixed, noises are caused in the detection data. In this case, if the radioactive labeling substance is used, for example, the quantitative analysis of the substance derived from living organism is not made correctly. Especially, if the labeling substance is spotted in high density, the quantitative analysis becomes simply bad.

Note that in order to make the cost for producing the biochemical analysis unit lower, it is preferable to produce the biochemical analysis unit effectively.

SUMMARY OF THE INVENTION

An object of the present invention is to provide a method for producing a biochemical analysis unit with which the generation of a noise is prevented and a biochemical analysis is carried out in high resolution.

Another object of the present invention is to provide a method for producing a biochemical analysis unit in which a radioactive energy or the luminescent light that are released from a spot are not mixed with those from the neighboring spots.

Still another objects of the present invention is to provide a method for producing the biochemical analysis unit effectively.

In order to achieve the object and the other object, a continuous substrate in which plural holes are formed and a continuous absorptive sheet formed of an absorptive material are piled during feeding. Then, the substrate and the absorptive sheet are pressed continuously or intermittently by pressing members perpendicularly to a feed direction. A part of the absorptive sheet is charged or fitted in the holes by pressing. The continuous substrate is formed of materials having characters for shielding an electromagnetic wave, especially a light. The continuous absorptive sheet is formed of porous material, for example.

The continuous biochemical analysis sheet is constituted of the continuous substrate and the continuous absorptive sheet. By cutting the continuous biochemical analysis sheet to have a predetermined size, plural biochemical analysis units are obtained.

An adhesive agent may be provided so as to adhere the continuous absorptive sheet to the continuous substrate. One of the press members that contacts to the substrate is heated at more than a glass transition temperature and lower than the melting points of the substrate, the adhesive agent and the absorptive sheet.

According to the method of producing the biochemical analysis unit of the present invention, as the continuous substrate and the continuous absorptive sheet are pressed perpendicular to the feeding direction, the plural biochemical analysis units are effectively produced. Further, as one of the pressing members is warmed, the absorptive material easily enters into the holes. In the biochemical analysis unit, as the absorptive material is charged in the plural holes, the radioactive ray and the light do not scatter which causes a noise in a detection data.

BRIEF DISCRIPTION OF THE DRAWINGS

The above objects and advantages of the present invention will become easily understood by one of ordinary skill in the art when the following detailed description would be read in connection with the accompanying drawings.

PREFERRED EMBODIMENTS OF THE INVENTION

Figure 1:
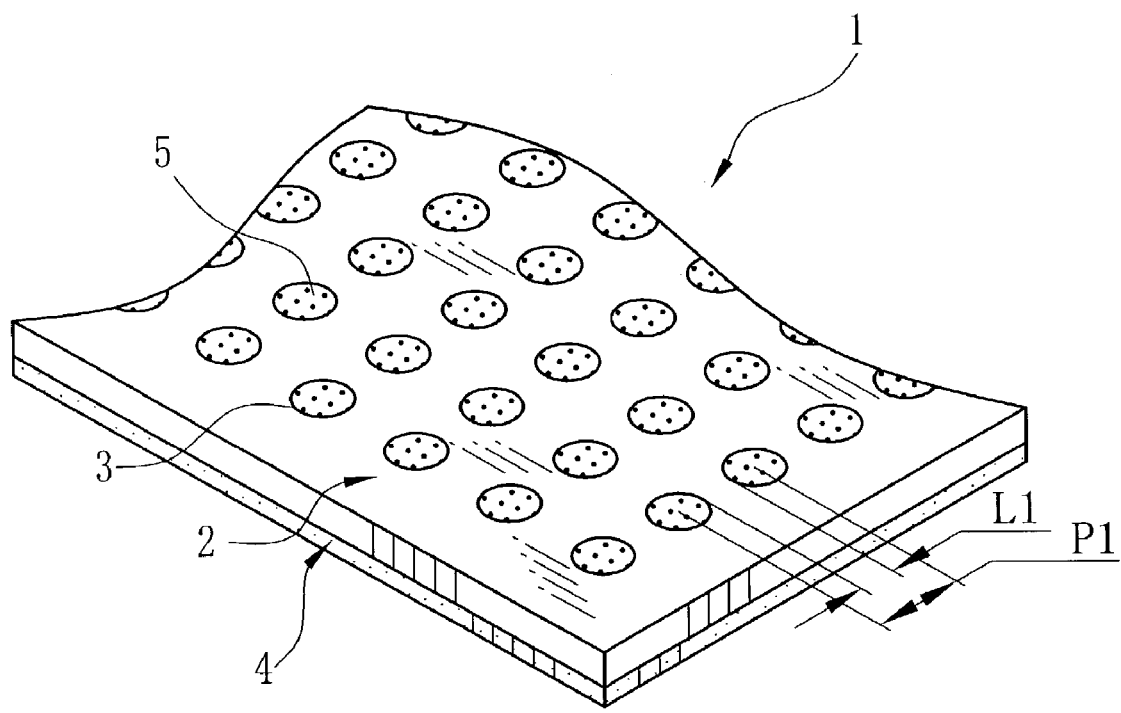
FIG. 1 is a perspective partial view of a biochemical analysis sheet of the present invention.

In FIG. 1, a biochemical analysis sheet 1 is constituted of a continuous substrate or continuous straight sheet 2 provided with plural holes 3 and a continuous porous sheet 4. The continuous porous sheet 4 is made of a porous material, and used as a continuous absorptive sheet whose part is charged in the hole 3 to form spot regions 5. On each of the spot regions 5 is spotted each kind of specific binding substances whose structure and characteristic are known. Thereafter the specific binding substance is processed and fixed to the porous material in the spot region 5.

The biochemical analysis sheet 1 is cut into biochemical analysis units, each of which has a predetermined number of spot regions 5.

When the biochemical analysis unit is used for the clinical examination, a substance derived from living organism is dropped on each of the spot regions 5 constructing a micro array. The specific binding substances are hybridized with a substance derived from living organism that is labeled with a labeling substance. As the specific binding substance, there are radioactive substance, luminescent substance, and chemniluminescent substance. Then after predetermined processing, a radioactive ray or a light is emitted from the labeling substance in the spot region 5.

As the continuous substrate 2, following materials are used, metal, ceramic, and the like, which does not pass the radioactive ray or a light, or which decreases the amount thereof. Further, the continuous substrate 2 can be made of a plastic in which the holes are easily formed. In this case, however, particles of metal or ceramic are contained in the plastic in order to decrease the amount of the radioactive ray or the light.

As the metal material for forming the continuous substrate 2, there are, for example, cupper, silver, gold, zinc, lead, aluminum, titanium, tin, nickel, cobalt, tantalum, or alloys, such as stainless, brass and the like.

As the plastic material there are, for example, polyolefin (polyethylene, polypropylene and the like), acryl resin (polystyrene, polymethylmethacrilate and the like), polyesters (polyvinyl chloride, polyvinylidene chloride, polyvinylidene fluoride, polytetrafluoro ethylene, polychlorotrifluoro ethylene, polycarbonate, polyethylene naphthalate, polyethylene terephthalate and the like), fatty acid polyamide (nylon-6, nylon-66 and the like), silicon resin (polyimide, polysulfone, polyphenylene sulfide, polydiphenyl siloxane and the like), phenol resin (noborac and the like), epoxy resin, cellulose acetate, cellulose (polyurethane, cellulose acetate, nitrocellulose and the like), copolymer (butadiene-styrene copolymer). A blend of these plastics may be also used.

As the particles contained in the plastics, there are metallic particles and a glass fiber. As the metallic particles, there are silicone dioxide, alumina, titanium dioxide, iron oxide, cupper oxide and the like.

As the ceramics material, there are alumina, zirconia, magnesia, quartz and the like. It is noted that the sorts of the above materials are not restricted in them.

In the biochemical analysis unit, the radioactive ray or the light emitted from the spot regions 5, when arriving at the neighboring spot regions 5 through the substrate 2, is decreased less than 1/5 and preferablely 1/10.

A transmission distance of the electric ray is in inverse proportion to the density of material in which the radioactive ray passes. Accordingly, when the labeling substance is a widely used radioisotope, such as $^{32}P$, $^{33}P$, $^{35}S$, $^{14}C$ and the like, the averaged density of the continuous substrate 2 is more than 0.6 g/cm$^3$, preferably 1-20 g/cm$^3$, and especially 2-10 g/cm$^3$. In this case, the continuous substrate 2 shields the radioactive ray emitted from the radioisotope in each spot region 5. Therefore the generation of noise in the detection data, which is caused from the scattering and transmission of the radioactive ray, is prevented.

The thickness of the continuous substrate 2 is 50-1000 μm, preferably 100-500 μm.

It is preferable that the holes 3 are formed at high density. Accordingly, the size of the holes 3 is less than 5 mm$^2$, preferably less than 1 mm$^2$, particularly 0.3 mm$^2$, and especially more than 0.001 mm$^2$.

A pitch P1 of the holes 3 that is defined as a distance between centers of neighboring holes 3 is determined to 0.05-3 mm. An interval L1 defined as a distance between edges of the neighboring holes 3 is determined to 0.01-1.5 mm. The density of number of the holes is determined to more than 10/cm$^2$, preferably more than 100/cm$^2$, particularly more than 500/cm$^2$, and especially 1000/cm$^2$. However, there is an upper limit. Namely, the density is preferable less than 100,000/cm$^2$, and especially 10,000/cm$^2$.

Note that the holes 3 may not be formed at a same pitch when the above conditions are filled. For example, the holes 3 in alignment in one direction may be alternately arranged in another direction perpendicular to the one direction. Further the holes 3 may be randomly formed. The holes 3 may be formed to have triangle, tetragonal, hexagonal, other polygonal, elliptic and other forms. Furthermore, the absorptive spot region 5 of the rectangular form which is very long in a longitudinal direction thereof may be formed in a stripe manner.

Figure 2A:
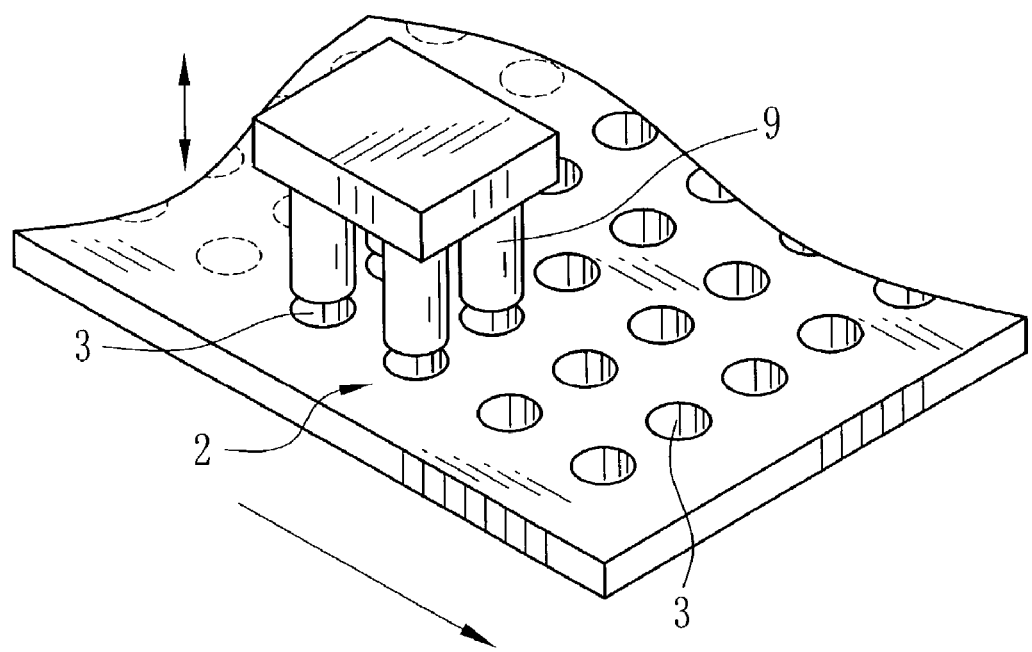
FIG. 2A is a perspective partial view of the continuous substrate, illustrating a situation that holes are formed with a pitch.

As shown in FIG. 2A, the holes 3 are formed with punches 9. Further, the holes 3 may be formed with discharging electrodes which are arranged at the pitch P1. In this case, the continuous substrate 2 is grounded and supplied in insulating fluid, such as oil, air, and the like, and thereafter the discharging electrodes are closed to the continuous substrate 2. When a high voltage is supplied to the electrodes, an electric discharge causes to heat the continuous substrate 2, whose parts confronting to the electrodes are evaporated to form the holes 3.

Figure 2B:
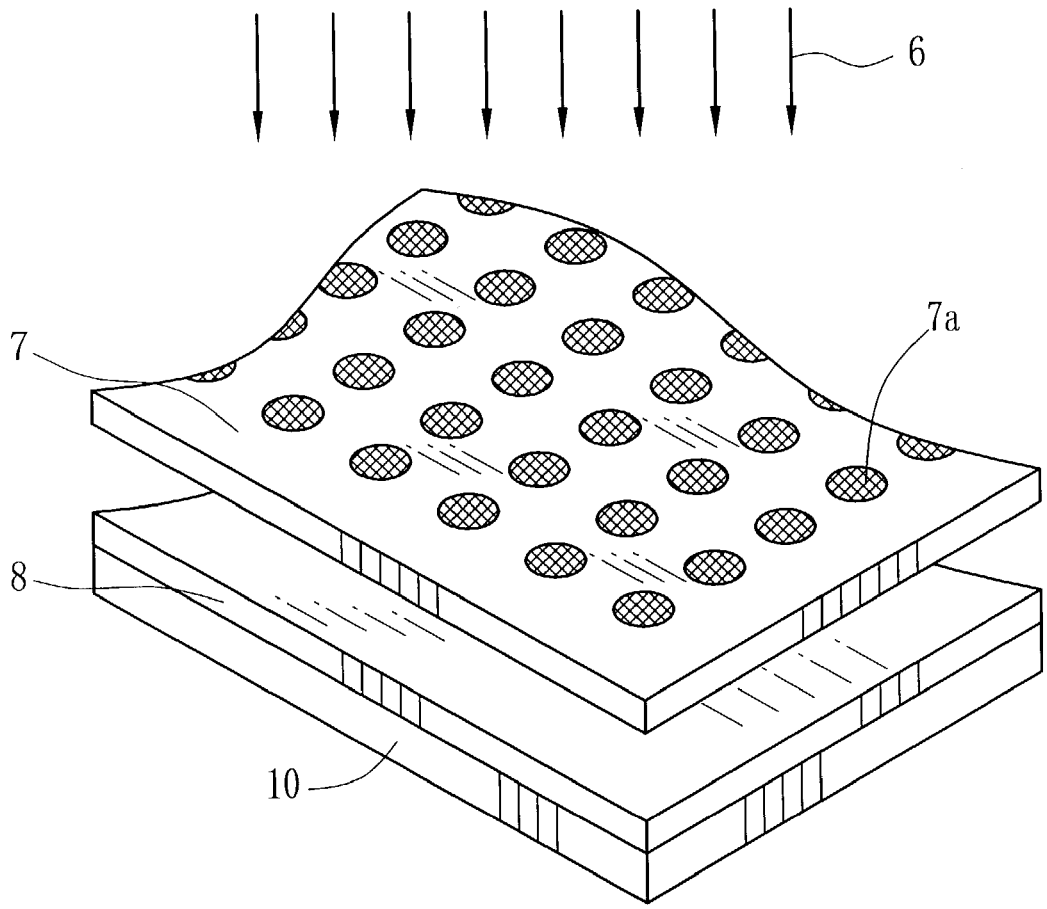
FIG. 2B is an explanatory view illustrating a method for forming the continuous substrate in a photo etching method.
Figure 3:
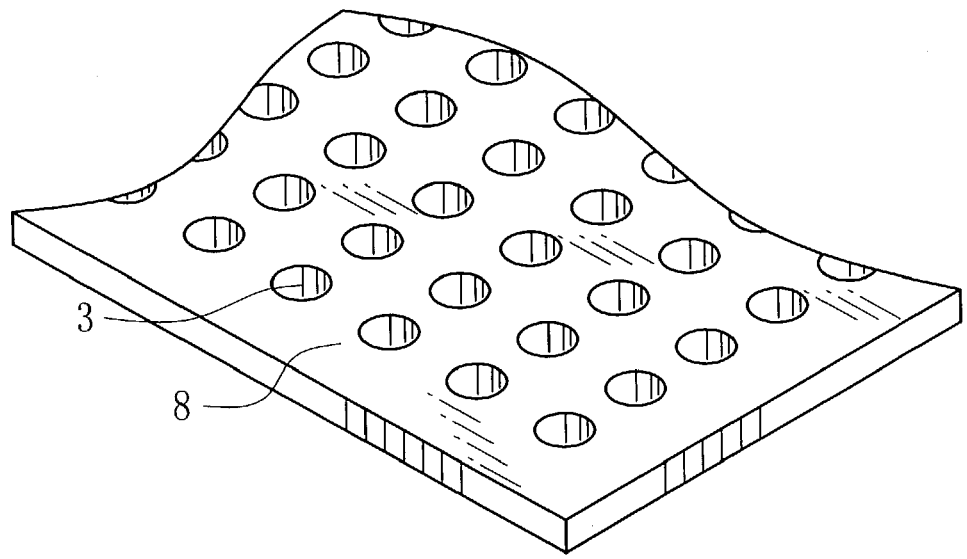
FIG. 3 is a perspective view of the continuous substrate which is made with the photo etching method in FIG. 2B.

The holes 3 in the continuous substrate 2 may be formed in making a photolithograph and etching. As shown in FIG. 2B, on the continuous support 10, there is a coating layer 8 formed by applying a light or ultraviolet ray curing agent. On the coating layer 8, a mask 7 having hole patterns 7a is piled. Then a light is illuminated through the mask 7 to the coating layer 8 to make the photolithograph. Thus part of the coating layer 8 around the hole patterns 7a is hardened. Thereafter, the coating layer 8 is inserted in an organic solvent to solve the other parts of the coating layer 8 that is not hardened. Thereafter, the coating layer 8 is removed from the support 10 to become the substrate in FIG. 3. Note that the support 10 is preferably formed of polyethylene, polypropylene, polyethylene terephthalate, polytetrafluoroethylene and the like.

It is preferable to use ultraviolet curable compounds as the coating layer 8. The ultraviolet curable compounds are produced from an optical polymerizer and a ultraviolet curable resin material. The optical polymerizer is, for example, hydrogen pulling type initiator (benzophenone initiator), radical fragmentation type initiator (acetophenone initiator, triazine initiator). Further, the ultraviolet curable resin material is acrylic acid esters (acrylic acid ethyl, acrylic acid butyl, acrylic acid 2-ethylhexil), methacrylic acid esters (methacrylic acid methyl, methacrylic acid ethyl, methacrylic acid butyl, ethylene glycol dimethacrylate), ester of high carbon alcohol and (metha-)acrylic acid (ethylene glycol di(meta) acrylate, 1,4-diclohexane diacrylate, dipentaerythritol tetra (meta)acrylate), pentaerythritol tri(meta)acrylate, trimethylolpropane tri(meta)acrylate, trimethylolethane tri(meta) acrylate, dipentaerithritol tetra(meta)acrylate, dipentaerythritol penta(meta)acrylate, pentaerythrytol hexa (meta)acrylate), 1,2,3-cyclohexane tetramethacrylate, polyurethane polyacrylate, polyester polyacrylate) and the like. These materials may be mixed to use.

As organic solvents used for etching there are ketones such as acetone, methylethylketone. However other solvents may be used if possible to solve the ultraviolet curing compounds. It is preferable that the continuous support 10 is affected in a supersonic wave in the etching liquid when etching is carried out.

When the continuous substrate 2 is made of metal, the holes 3 are formed with electrolytic etching. A resist is applied on the metallic substrate, and an exposure is made with a photomask pattern. For example, a metal plate and a platinum are used as an anode and a cathode, and set into solutions of strong acids, such as sulfuric acid, fluoric acid, phosphoric acid and the like. Then after forming the holes 3, the resist on the metallic substrate is removed.

Further, high power laser beam may be emitted to form the plural holes on the continuous substrate. In this case, when the laser beam is scanned on the continuous substrate, the holes are formed. The high power laser beam is exima laser, YAG laser and the like. The holes formed in the continuous substrate may be through-holes.

Figure 4:
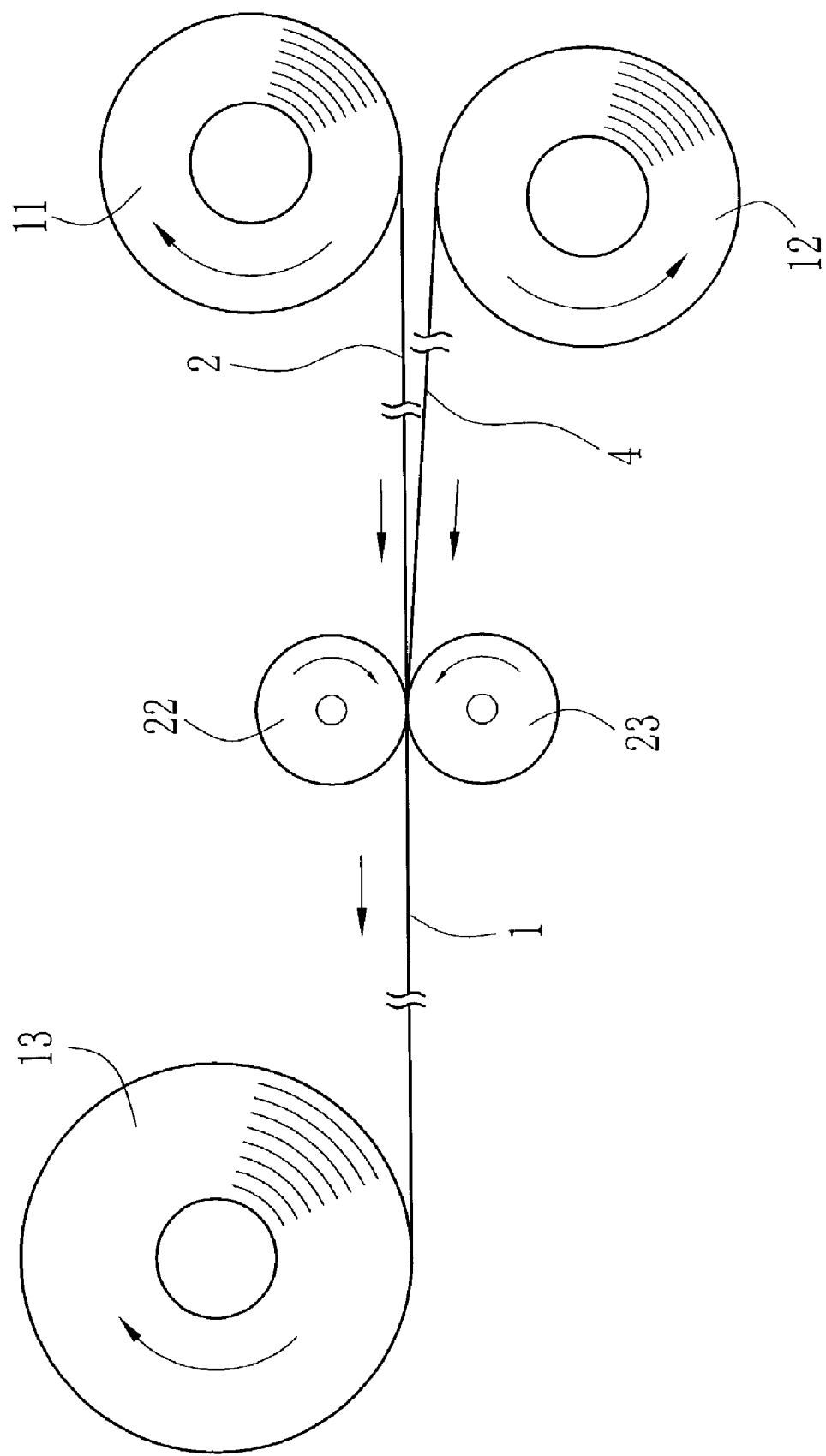
FIG. 4 is a diagrammatic sectional view illustrating the situation of pressing a porous sheet to the continuous substrate with a roller pair.

The continuous porous sheet 4 is made with a film producing apparatus (not shown). In the film producing apparatus, a solution (hereafter dope), in which the polymer as a staff of the porous material is solved to a solvent, is cast on a substrate. The dope is thereafter gradually washed in water and dried after immersed in a bath containing solvent and nonsolvent of the polymer. Thus the continuous porous sheet 2 is rolled to form a porous sheet roll 12, as shown in FIG. 4.

The porous material may be organic or inorganic material, or may be also organic/inorganic complex.

The organic porous material is carbon porous material (activated carbon) and porous material of which a membrane filter is formed. Preferably, the porous material for forming the membrane filter is polymers which can be solved to a solvent for forming the porous material: cellulose derivatives (nitro cellulose, reproduced cellulose, cellulose acetate, acetylic cellulose, acetylic propylic cellulose, and the like), fatty group polyamides (nylon-6, nylon-66, nylon-4,10 and the like), polyolefins (polyethylene, polypropyrene, and the like), polymers including chlorine (polychloride vinyl, polychloride vinylidene and the like), fluoride resins (polyfluorovinylidene, polytetrafluoride and the like), polycarbonate, polysulfone, arginic acid and derivatives thereof (calcium arginate, arginic acid/polylisine polyion complex and the like), collagen and the like. Further copolymer of these polymers may be used.

The inorganic porous material is, preferably, metal (platinum, gold, iron, silver, nickel, aluminum and the like), oxide of metal (alumina, silica, titania, zeolite and the like), salt of metal (hydroxyapertite, calcium sulfide and the like), and their complexes.

In order to make the porous material stronger, unsolvable fiber-like materials may be mixed to the porous material. As the fiber-like material, there are cellulose, glass fiber, metallic fiber and the like, which are hardly solved to the solvent.

Further, a continuous absorptive sheet may be made of a fiber material, which is, for example, cellulose derivatives, fatty acid polyamides and the like.

Figure 5:
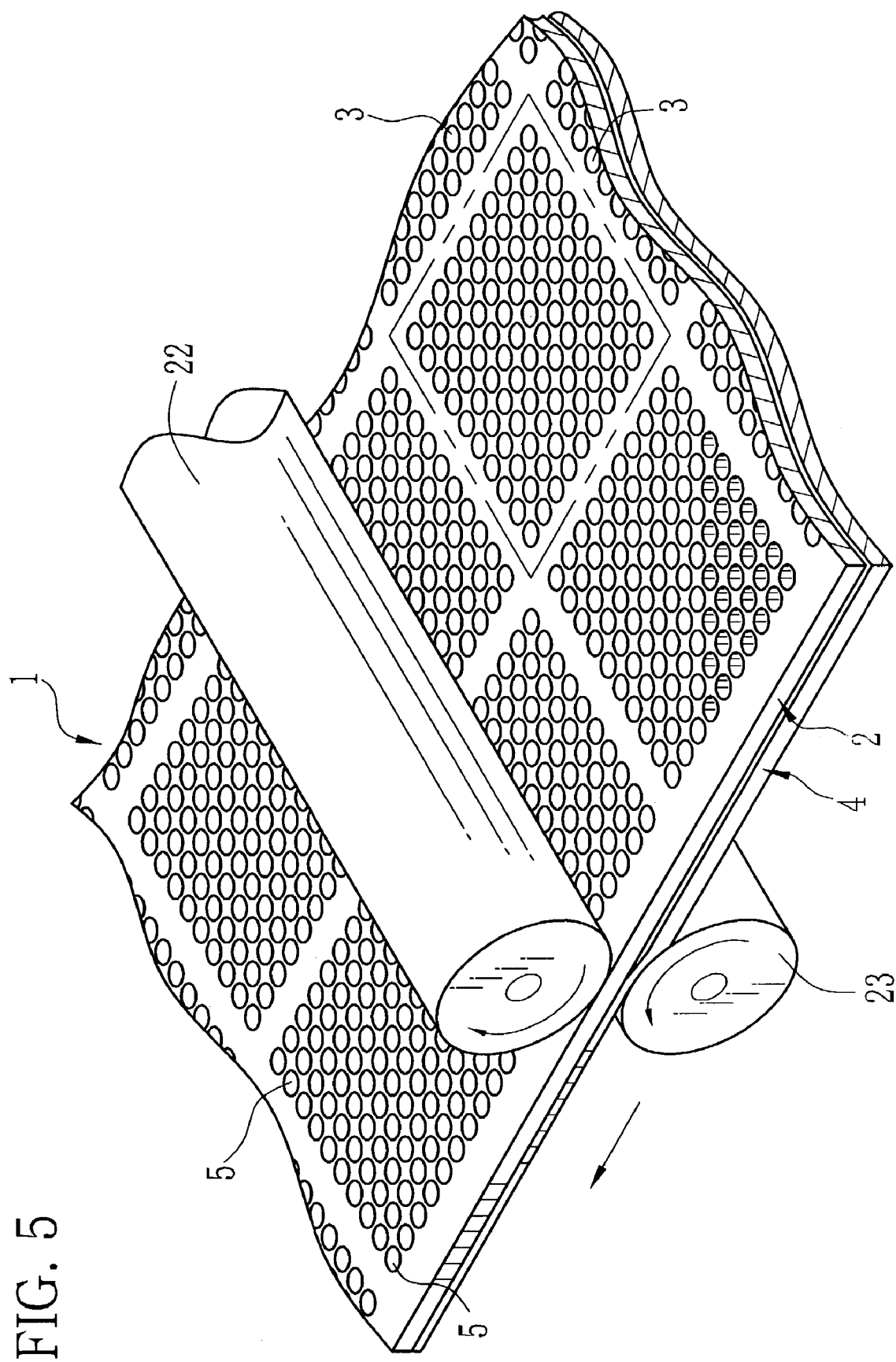
FIG. 5 is a partial perspective view of FIG. 4.

In FIGS. 4 and 5, the continuous substrate 2 and the continuous porous sheet 4 are unwound from a substrate roll 11 and a porous sheet roll 12 respectively, and continuously fed by a feeding device (not shown) into a press station between a press roller 22 and a the back up roller 23. Thereby the press roller 22 and the back up roller 23 continuously press the continuous substrate 2 and the continuous porous sheet 4 to form the biochemical analysis sheet 1. Then the biochemical analysis sheet is rolled as an analysis sheet roll 13.

In the biochemical analysis sheet 1 is formed a large number of the spot region 5 under which part of the porous sheet 4 is charged in the holes 3. In the spot regions 5, many kinds of the specific binding substance labeled with a labeling substance are dropped. Note that part of the continuous porous sheet 4, which is not used for charging and remains on the substrate 2, may be removed in known method before and after the dropping the specific binding substance.

Figure 6A:
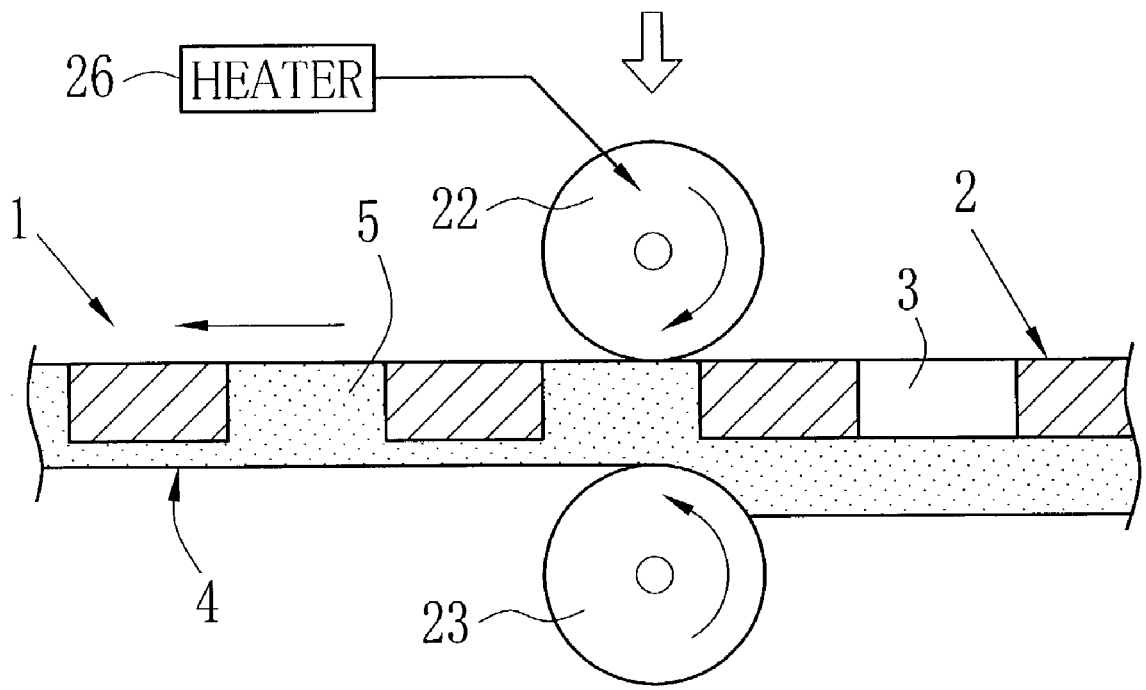
FIG. 6A is a diagrammatic sectional view illustrating the situation of pressing a continuous porous sheet to a continuous substrate with the roller pair.
Figure 6B:
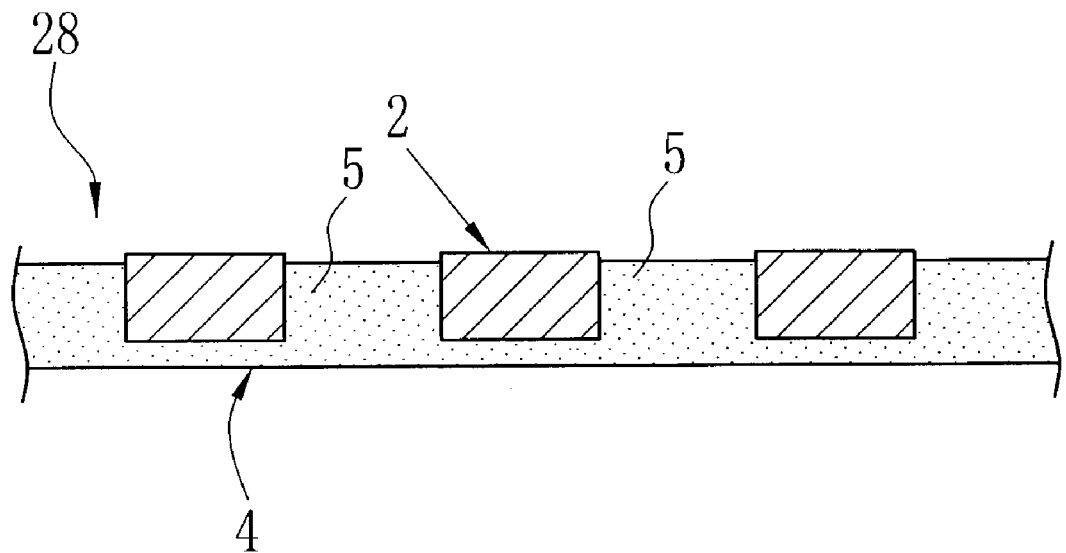
FIG. 6B is a partial sectional view of another embodiment of the biochemical analysis unit, wherein the porous sheet is retracted from the substrate.

As shown in FIG. 6A, the press roller 22 is heated with a heater 26. In this case, the continuous porous sheet 4 becomes softened, and a part thereof is more easily pressed into the holes 3 to form the absorptive spot region 5. Preferably, as shown in FIG. 6B, the absorptive spot region 5 is retracted from a surface of the continuous substrate 2 of a biochemical analysis sheet 28.

Figure 7:
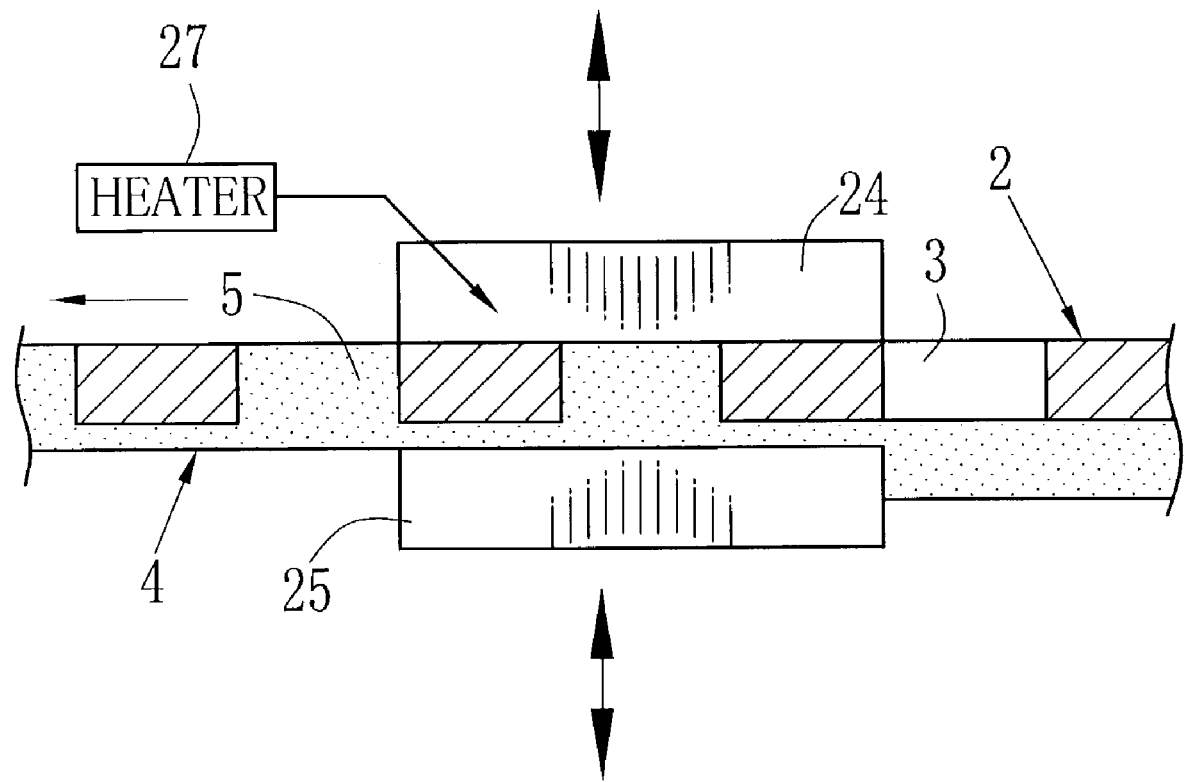
FIG. 7 is an explanatory view of intermittently pressing the continuous porous sheet to the continuous substrate with pressing plates.

As shown in FIG. 7, the continuous substrate 2 and the continuous porous sheet 4 may be intermittently pressed. In this case, the continuous substrate 2 and the continuous porous sheet 4 are intermittently fed to the press station. In the press station, the continuous substrate 2 and the continuous porous sheet 4 are intermittently pressed with press plates 24, 25 which are movable up and down. The press plate 24 is heated with a heater 27. Note that the large size of the rectangular substrate and the large size of the rectangular porous sheet may be used for forming a large size of the biochemical analysis unit. In this case, the continuous substrate and the continuous porous sheet are previously set to the press station.

Further, the continuous substrate 2 and the continuous porous sheet 4 are simultaneously pressed in a widthwise direction when in carrying out the intermittently pressing. However, each area surrounded with a chain double-dashed line may be pressed. In this case, the porous sheet can be uniformly charged in the holes 3.

In FIGS. 6A-7, in order to prevent the porous sheet 4 from adhering to the back up roller 23 or the press plate 25 to brake the porous sheet 4, it is preferable that a surface of the back up roller 23 or the press plate 25 is processed. For example, a surface roughness (arithmetic mean) of the back up roller 23 or the press plate 25 may be more than 0.3 μm. Otherwise, the surface of the back up roller 23 or the press plate 25 may be coated with a hydrophobic resin. Otherwise, plating of the surface of the back up roller 23 or the press plate 25 with chromium or nickel containing hydrophobic resin may be carried out.

Note that a part surrounded with a chain double-dashed line in FIG. 5 is cut after producing the biochemical analysis sheet 1 to become the one biochemical analysis unit. The biochemical analysis unit has 10×10 of the spot region 5 for detecting 100 substances derived from living organism. Note that the cutting of the biochemical analysis sheet is carried out before or after applying the specific binding substance.

Figure 8:
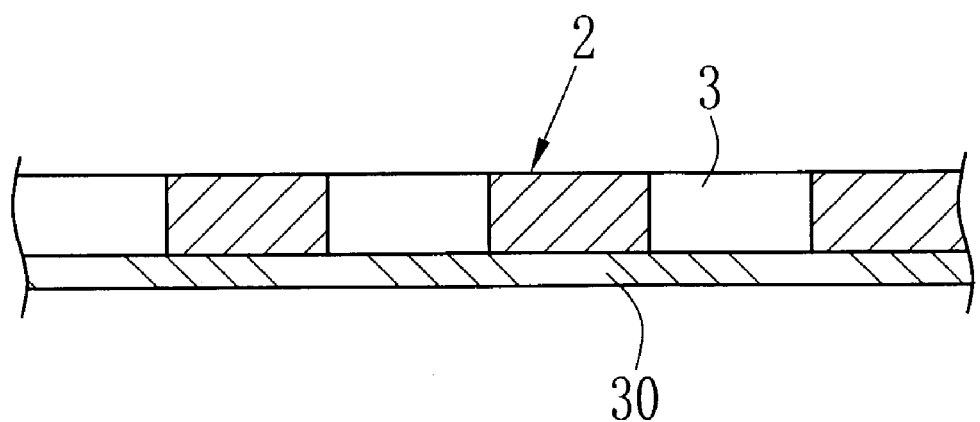
FIG. 8 is a sectional view of the continuous substrate, one of whose surface is coated with an adhesive layer.

In FIG. 8, an adhesive layer 30 is previously formed on a surface of the substrate 2. The adhesive layer 30 fixes the porous material into the hole 30. It is preferable that the adhesive layer 30 is formed of styrene butadiene rubber, acrylonitrile butadiene rubber. Methods for forming the adhesive layers is, for example, dip coating, air knife coating, blade coating, and the like. Further, a continuous adhesive sheet may be used, which is supplied between the continuous substrate 2 and the continuous porous sheet 4, and they are pressed. Further, before coating with the adhesive layer, the surface of the continuous substrate 2 may be processed (for example, oxidized). When the continuous substrate 2 is metal, the surface thereof is oxidized in anodic oxidation processing. In the anodic oxidation processing, anode is inserted in solution of sulfuric acid, phosphoric acid, or chromic acid, and then the voltage is urged to carry out oxidization. When the continuous substrate 2 is made of plastic, particles of metal oxides are provided. When the continuous substrate 2 is ceramics, it may be metal oxide.

When the adhesive layer 30 is formed on the continuous substrate 2, it is prevented after pressed by the press roller 22 and the back up roller 23 that the continuous porous sheet 4 peels from the continuous substrate 2. When the press roller 22 or the back up roller 23 is heated, not only the continuous porous sheet 4 becomes warmer, but also the adhesive layer 30. Accordingly, the effect of the adhesive layer becomes larger. In this case, it is preferable that the temperature of the press roller 22 is higher than the glass transition temperature, and lower than the melting points of all of the adhesive layer 30, the continuous substrate 2, and the continuous porous sheet 4. When the temperature of the press roller 22 is lower than the glass transition temperature, the adhesive layer 30 is not effective. Further, when the temperature of the press roller 22 is higher than the melting points of all of the adhesive layer 30, the continuous substrate 2, and the continuous porous sheet 4, then the continuous substrate 2 and other members are easily deformed.

Note that a percentage of void of the continuous porous sheet 4 is 10-90%, and the average pore diameter of the holes is 0.1-50 μm.

In order to accelerate the penetrating of the specific binding substance into the porous material, the surface of the porous material is often processed to become hydrophilic. For example, when the continuous substrate 2 is made of conductive material, such as metal, the continuous substrate 2 is grounded. Further, when the continuous substrate 2 is made of insulating material, such as plastics and the ceramics, the continuous substrate 2 is disposed on the conductive material which is grounded. Then the electrodes supplied in high voltage of alternating current are confronted to the continuous substrate 2.

In order that the absorption of the specific binding substances in the porous material may be accelerated, it is preferable that the porous material contains the surface-active agent. As the surface-active agents, there are anion types, cation types and fluoride types: for example, potassium dodecylbenzenesulfonate, saponin, potassium p-tert-octylphenoxyethoxyethylsulfonate, nonylphenoxy-polyethoxy-ethanol; fluoride type surface-active agents which are disclosed in Japanese Patent Laid-Open Publications No. S62-170950, S63-188135 and U.S. Pat. No. 5,380,644; and polyalkyreneoxide and anion type surface-active agents which are disclosed in Japanese Laid-Open publication No. H6-301140.

According to the porous material in the porous material, a contact angle of water is preferably less than 60°, especially less than 50°.

Preferably, as shown in FIG. 6B, the porous material in the spot region 5 is retracted from the surface of the substrate 2. Thereby, the spotting of the specific binding substances on the porous material is more easily carried out. And the specific binding substance flows onto neither the surface of the substrate 2 nor the other absorptive regions 5.

As the specific binding substance, polynucleotide and oligonucleotide are conventionally used to forming the micro array. For example, cDNA, a part of cDNA, polynucleotide (PCR products) prepared in PCR method (for example, EST and the like), and synthesized nucleotide. Note that artificial nucleotide, that is, peptide nucleic acids (PNA) and derivatives thereof in which the phosphodiester bond of DNA is transformed into the peptide bond. Further, the specific binding substances spotted in the absorptive regions of the above embodiment may bind with the substance derived from a living organism such as a hormone, tumormarker, enzyme, antibody, antigen, abzyme, other protein, a nucleic acid, cDNA, DNA, RNA, or the like, whose sequence, base length, composition and the like are known.

Further, as described in U.S. Pat. No. 5,807,522, the specific binding substances are spotted onto the absorptive spot regions 5 in spotting method and ink jetting method. In the spotting method, the specific binding substances are applied to a pin to transmit to the porous material. In the ink jetting method, a liquid containing the specific binding substances is jetted onto the porous material in the spot regions 5.

Preferably, the specific binding substances are bound in heat or illumination of the ultra-violet ray with the substances derived from living organism that is labeled with the labeling substance. As the reactions, there are hybridization of cDNA, antigene-antibody reaction, receptor-ligand and the like.

The labeling substance contains at least one of a radioactive labeling substance, a fluorescent labeling substance and a chemiluminescent labeling substance.

Figure 9A:
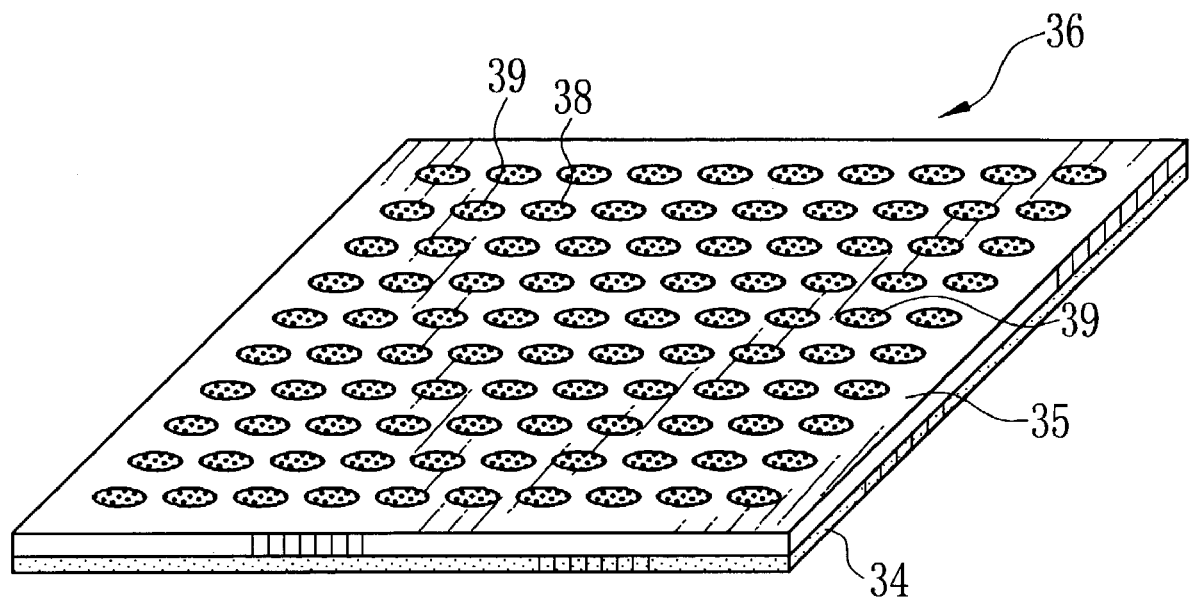
FIG. 9A is a perspective view of a stimulating phosphor sheet.

In case that the substances derived from living organism is labeled with the radioactive labeling substance, a stimulable phosphor sheet 36 in FIG. 9A is used for analysis. The stimulable phosphor sheet 36 includes a stimulable phosphor layer 34 made of a stimulable phosphor and a base 35 in which holes 38 are formed at the pitch the same as in the biochemical analysis unit. The holes 38 are filled with a part of the stimulable phosphor layer 34 to form the phosphor spot region 39. Further, for carrying out the analysis the stimulabel phosphor sheet may be used, in which the stimulabel phosphor may be uniformly applied to the phosphor spot region 39.

Figure 9B:
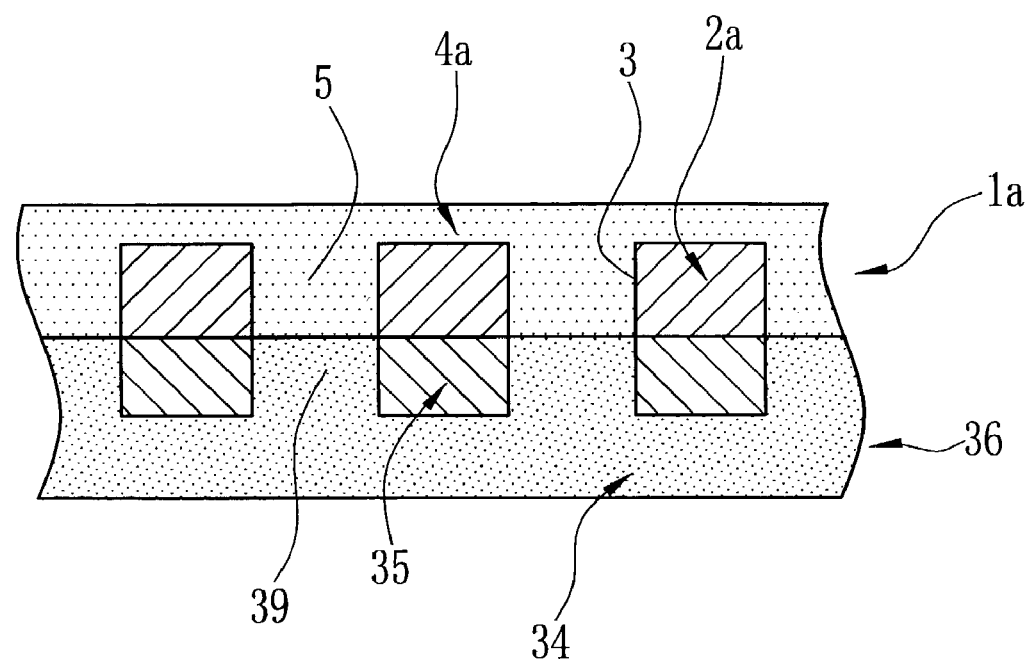
FIG. 9B is a sectional view of the stimulating phosphor sheet and the biochemical analysis unit which are overlaped.

As shown in FIG. 9B, the stimulable phosphor sheet 36 is piled on the biochemical analysis unit 1a. The biochemical analysis unit 1a is formed by cutting the biochemical analysis unit 1 into a tip, and has a substrate 2a and a porous sheet 4a. Thereby the porous spot region 5 of the biochemical analysis unit 1a confronts to a phosphor spot region 39 of the stimulable phosphor sheet 37. Accordingly, the phosphor spot region 39 is exposed at a predetermined time to the radioactive ray emitted from the radioactive labeling substance. Thus energy of the radioactive ray is accumulated in the stimulable phosphor sheet 36 in the phosphor spot region 39.

Thereafter the stimulable phosphor sheet 36 is set in an analyzing system (see, FIG. 10) and illuminated in a visible ray. Then the stimulable phosphor is exited and emits a light whose wavelength corresponds to the accumulated energy.

The stimulable phosphor is for example:
1) Japanese Patent Laid-Open Publication No. S55-12145 discloses alkaline earth material fluoride halide phosphors $(Ba_{1-x}M^{2+}_x)FX:yA$ (herein $M^{2+}$ is at least one of alkaline earth material Mg, Ca, Sr, Zn and Cd, X is at least one halogen of Cl, Br and I, and A is Eu, Tb, Ce, Tm, Dy, Pr, He, Nd, Yb and Er; $0 \leq x \leq 0.6$, $0 \leq y \leq 0.2$;
2) Japanese Patent Laid-Open Publication No. H2-276997 discloses alkaline earth material fluoride halide phosphors SrFX:Z (herein X is halogen, at least one of Cl, Br and I, and Z is Eu or Ce);
3) Japanese Patent Laid-Open Publication No. S59-56479 discloses europium activated complex halogen phosphors $BaFX.xNaX':aEu^{2+}$ (herein each X and X' is halogen, at least one of Cl, Br and I; $0<x \leq 2$, $0<a \leq 0.2$);
4) Japanese Patent Laid-Open Publication No. 58-69281 discloses cerium activated metal Oxyhalide, MOX:xCe (herein M is at least one of metals, Pr, Nd, Pm, Sm, Eu, Tb, Dy, Ho, Er, Tm, Yb and Bi, X is halogen, one or both of Br and I; $0<x<0.1$);
5) Japanese Laid-Open Publications No. 60-101179 and 60-90288 disclose cerium activated rear earth material oxyhalide phosphors LnOX:xCe (herein Ln is at least one of rear earth elements Y, La, Gd and Lu, X is at least one of halogens Cl, Br and I; $0<x \leq 0.1$); and
6) Japanese Patent Laid-Open Publication No. S59-75200 discloses europium activated complex halide phosphor, $M^{(2)}FX.aM^{(1)}X'.bM'^{(2)}X''_2.cM^{(3)}X'''_3.xA:yEu^{2+}$ (herein $M^{(2)}$ is at least one of alkaline earth materials Li, Na, K, Rb and Cs, $M'^{(2)}$ is at least one of Be and Mg, $M^{(3)}$ is at least one of Al, Ga, In and Tl, A is at least one of oxides of metal, X is at least one of halogens Cl, Br and I, each X', X'' and X''' is one of halogens F, Cl, Br and I; $0 \leq a \leq 2$, $0 \leq b \leq 10^{-2}$, $0 \leq c \leq 10^{-2}$, $a+b+c \geq 10^{-2}$, $0<x \leq 0.5$, and $0<y \leq 0.2$).

Figure 10:
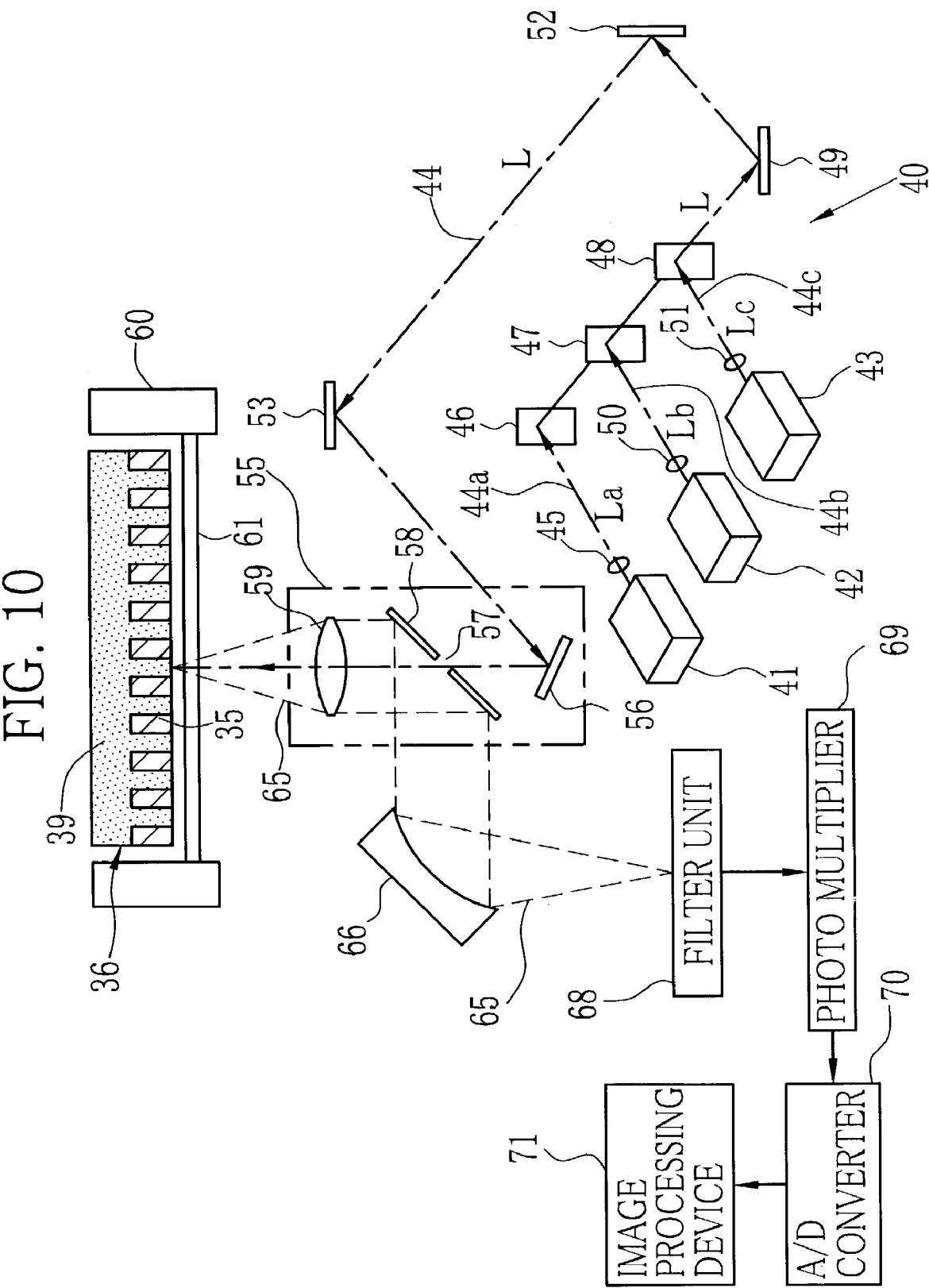
FIG. 10 is a schematic diagram of an analyzing system for carrying out a biochemical analysis by detecting an emission light from the stimulating phosphor sheet.

In FIG. 10, the data analysis system 40 is used for making the analysis of the substance derived from living organism. When the biochemical analysis is carried out, then a stimulable phosphor sheet 36 is previously piled on the biochemical analysis unit 1a to expose the stimulable phosphor sheet 36. The exposed stimulable phosphor sheet 36 is set onto the glass plate 61 of a stage 40. Thereby the phosphor spot region 39 confronts to the glass plate 61.

The data analysis system 40 includes first, second and third laser sources 41, 42, 43. The first laser source 41 is constructed of a semiconductor laser, and emits a laser beam 44a having wavelength of 640 nm. The second and third laser sources 42, 43 are constructed of second harmonic generation elements and emits a laser beam 44b having wavelength of 532 nm and a laser beam 44c having wavelength of 473 nm, respectively.

The scanner includes further first and second diachronic mirrors 47, 48 which selectively reflect the laser beams 44a, 44b, and 44c.

A laser beam 44a emitted from the first laser 21 is formed through a collimator lens 45 into a parallel beam, and is reflected by a mirror 46. A first diachronic mirror 47 and the second diachronic mirror 48 transmit the laser beam 44a. A laser beam 44b emitted from the second laser 42 is formed through a collimator lens 50 to be a parallel beam, and reflected by the first diachronic mirror 47. Then, the second diachronic mirror 48 transmits also the laser beam 44b. A laser beam 44c emitted from the third laser 43 passes through a collimator lens 51 to be a parallel beam, and reflected by the second diachronic mirror 48.

Thereafter, each of the laser beams 44a, 44b, 44c passes as an exiting beam 44 on an optical axis L in a light path and is reflected by mirror 49 and 52.

Downstream of the mirror 52, a perforated mirror 58 is disposed in the optical path. In a center of the perforated mirror 58 is formed a hole 57 through which the exiting beam 44 passes. Then the exiting beam 44 is reflected by a concave mirror 59 and enters into an optical head 55.

The optical head 55 includes a mirror 56 and an aspherical lens 59. After entering into the optical head 55, the exiting beam 44 is reflected by the mirror 56, and condensed by the aspherical lens 59 onto the stimulable phosphor sheet 36 on the glass plate 61. Thereby a fluorecent light 64 is discharged from the phosphor spot region 39.

The fluorescent light 65 is formed by the aspherical lens 59 into a parallel light, and reflects on the perforated mirror 58. Then the fluorescent light 65 reflects on a concave mirror 66 and passes through a filter unit 68. Thereafter, the fluorescent light 65 is detected by a photo multiplier 69, which generates a detection signal. The detection signal is transformed into a detection data in an A/D converter 70. The detection data is sent to an image processing device 71. The image processing device 71 processes the detection data to display an image formed on a display (not shown) in accordance with the detection data. Note that the optical head 55 is moved by a scanning mechanism (not shown) such that each of the phosphor spot region 39 of the stimulable phosphor sheet 36 is entirely scanned.

Embodiment (1) Produce of Substrate Having Through-Holes

A continuous SUS 304 sheet has a width 80 mm and a thickness of 100 µm. 10×10 circular holes whose radius is 0.2 mm are formed in the SUS 304 sheet with etching. A pitch and an interval between neighboring holes is 0.3 mm and 0.1 mm, respectively.

(2) Prepare of Porous Structure

| | |
|---|---|
| Nylon-66 (Aldrich Chemical Corporation) | 14 part by weight |
| Formic acid | 66 part by weight |
| Water | 20 part by weight |

Above materials are solved to prepare a solution for supplying for the porous material. The solution is cast on the polyester sheet with a casting coaster to have thickness of 160 µm. Then, the polyester sheet in which the coating layer is formed is immersed in a 40% formic acid bath to form the extremely small holes. Thereafter, the polyester sheet is washed in water and dried. Then the coating layer is removed from the polyester sheet such that the polyester sheet is obtained as the porous material sheet. Herein an average pore diameter is 0.5 µm.

(3) Forming of Biochemical Analysis Unit

The continuous substrate obtained in the process (1) and the continuous porous material sheet obtained in the process (3) are overlapped and continuously fed between the press roller and the backup roller. The press roller is heated at 150° C., and the substrate and the porous material sheet are continuously pressed in a pressure 400 kgf/cm$^2$ to obtain a biochemical analysis sheet.

Then a fragment of chain nucleic acid (specific binding substance) is dropped on and fixed to each of the absorptive spot regions of the biochemical analysis sheet. Thereafter, the biochemical analysis sheet is cut into tips having a predetermined size to obtain the plural biochemical analysis units.

(4) Estimation of Biochemical Analysis Unit

The biochemical analysis unit is supplied in a solution to carry out hybridization. The solution contains a radioactive labeling substance by which the fragment of chain nucleic acid complementary to the specific binding substance is labeled.

After withdrawing the biochemical analysis unit from the aqueous solution, it is washed in water and dried. A stimulable phosphor sheet is overlapped on the biochemical analysis unit to make an exposure. And operation of radio autography is carried out in a room temperature. Then, a radioactive data can be read out from the stimulable phosphor sheet in high resolution and high sensitivity.

Various changes and modifications are possible in the present invention and may be understood to be within the present invention.

What is claimed is:

1. A method for producing a biochemical analysis unit including a substrate having plural holes and an absorptive material provided in said holes, said method comprising steps of:

supplying a continuous substrate and a continuous absorptive sheet from supply rolls to a press station, said holes being formed in said continuous substrate, said continuous substrate being formed of materials for shielding a radioactive ray and a light, said continuous absorptive sheet being formed of said absorptive material;

pressing said continuous substrate and said continuous absorptive sheet at said press station, a part of said continuous absorptive sheet being charged in each of said holes of said substrate so as to form a biochemical analysis sheet; and cutting said biochemical analysis sheet to obtain said biochemical analysis unit.

2. A method as described in claim 1, wherein said continuous substrate and said continuous absorptive sheet are fed intermittently, and the pressing by a pair of press plates is carried out while the feeding stops.

3. A method as described in claim 2, wherein one of surfaces of said continuous substrate is coated with an adhesive agent to adhere said continuous absorptive sheet to said continuous substrate, said adhesive agent contains at least one of styrene-butadiene rubber and acrylonitrile-butadiene rubber.

4. A method as described in claim 2, wherein a continuous adhesive agent sheet is positioned between said substrate and said absorptive sheet before pressing, said continuous adhesive sheet adheres said continuous absorptive sheet to said continuous substrate.

5. A method as described in claim 4, wherein said one press plate which contacts to said continuous substrate is heated, and a heating temperature of said press plates is higher than a temperature of glass transition temperature and lower than melting points of said adhesive agent, said continuous substrate and said continuous absorptive sheet.

6. A method as described in claim 5, wherein a surface roughness of said other press plate which contacts to said continuous absorptive sheet is more than 0.3 μm.

7. A method as described in claim 5, wherein a surface of said other press plate which contacts to said continuous absorptive sheet is coated with a hydrophobic resin or by plated with nickel or chromium containing said hydrophobic resin.

8. A method as described in claim 2, wherein said absorptive material in said holes is retracted from at least one of said surface of said substrate.

9. A method as described in claim 2, wherein said holes formed in said substrate are arranged at a predetermined pitch.

10. A method as described in claim 9, wherein said hole has a circular shape.

11. A method as described in claim 1, wherein the feeding of said continuous substrate and said continuous absorptive sheet are carried out continuously, and the pressing by press roller pair is carried out.

12. A method as described in claim 11, wherein one of surfaces of said continuous substrate is coated with an adhesive agent to adhere said continuous absorptive sheet to said continuous substrate, said adhesive agent contains at least one of styrene-butadiene rubber and acrylonitrile-butadiene rubber.

13. A method as described in claim 11, wherein a continuous adhesive agent sheet is positioned between said substrate and said absorptive sheet before pressing, said continuous adhesive sheet adheres said continuous absorptive sheet to said continuous substrate.

14. A method as described in claim 12, wherein said one press roller which contacts to said continuous substrate is heated, and a temperature of said press rollers is higher than a temperature of glass transition temperature and lower than melting points of said adhesive agent, said continuous substrate and said continuous absorptive sheet.

15. A method as described in claim 14, wherein a surface roughness of said other press roller which contacts to said continuous absorptive sheet is more than 0.3 μm.

16. A method as described in claim 14, wherein a surface of said other press roller which contacts to said continuous absorptive sheet is coated with a hydrophobic resin or by plated with nickel or chromium containing said hydrophobic resin.

17. A method as described in claim 11, wherein said absorptive material in said holes is retracted from at least one of said surface of said substrate.

18. A method as described in claim 11, wherein said holes formed in said substrate are arranged at a predetermined pitch.

19. A method as described in claim 18, wherein said hole has a circular shape.

20. A method for producing a biochemical analysis unit including a unit base having plural holes and an absorptive material provided in said holes, said method comprising steps of:
  supplying a continuous substrate from first supply roll to a press station, said holes being formed in said continuous substrate, said continuous substrate being formed of materials for shielding a radioactive ray and a light;
  supplying a continuous absorptive sheet to a press station from second supply roll which is different from said first supply roll, said continuous absorptive sheet being formed of said absorptive material;
  pressing said continuous substrate and said continuous absorptive sheet at said press station, a part of said continuous absorptive sheet being charged in each of said holes of said substrate so as to form a biochemical analysis sheet; and
  winding said biochemical analysis sheet to form a roll for use in making the biochemical analysis unit.

21. A method as described in claim 20, wherein a surface of said absorptive material is retracted from a surface of said substrate.

* * * * *